United States Patent [19]
Palmer et al.

[11] Patent Number: 5,840,043
[45] Date of Patent: Nov. 24, 1998

[54] JAW ASSEMBLY FOR AN ENDOSCOPIC INSTRUMENT

[75] Inventors: Matthew A. Palmer, Miami; Charles R. Slater, Fort Lauderdale; Vincent A. Turturro, Miramar; Matthew S. Solar, Cooper City; Saul Gottlieb, Miami; Jose L. Francese, Miami Springs; John Jairo Damarati, Miami, all of Fla.

[73] Assignee: Symbiosis Corporation, Miami, Fla.

[21] Appl. No.: 888,567

[22] Filed: Jul. 7, 1997

Related U.S. Application Data

[63] Continuation of Ser. No. 440,327, May 12, 1995, Pat. No. 5,507,296, which is a continuation-in-part of Ser. No. 189,937, Feb. 1, 1994, Pat. No. 5,542,432.

[51] Int. Cl.$^6$ .............................. A61B 10/00; A61B 17/28
[52] U.S. Cl. ............................................................. 600/564
[58] Field of Search .................................. 600/562, 564, 600/567; 606/167, 170, 205–208

[56] References Cited

U.S. PATENT DOCUMENTS

| | | | |
|---|---|---|---|
| 3,001,522 | 9/1961 | Silverman | 600/567 |
| 3,175,554 | 3/1965 | Stewart | 600/567 |
| 3,404,677 | 10/1968 | Springer | 600/564 |
| 3,989,033 | 11/1976 | Halpern et al. | 600/567 |
| 3,989,049 | 11/1976 | Yoon | 128/831 |
| 4,200,111 | 4/1980 | Harris | 600/564 |
| 4,393,872 | 7/1983 | Reznik et al. | 604/151 |
| 4,600,007 | 7/1986 | Lahodny et al. | 606/205 |
| 4,669,471 | 6/1987 | Hayashi | 606/205 X |
| 5,052,402 | 10/1991 | Bencini et al. | 600/564 |
| 5,281,230 | 1/1994 | Heldmueller | 606/127 |
| 5,334,198 | 8/1994 | Hart et al. | 606/52 |
| 5,352,235 | 10/1994 | Koros et al. | 606/174 |
| 5,562,699 | 10/1996 | Heimberger et al. | 600/564 |

Primary Examiner—John P. Lacyk
Assistant Examiner—Samuel Gilbert
Attorney, Agent, or Firm—David P. Gordon; David S. Jacobson; Thomas A. Gallagher

[57] ABSTRACT

An endoscopic instrument is provided with a hollow tube, first and second end effectors coupled to the hollow tube and having arms biased away from each other, a cylindrical member slidably disposed over the hollow tube, a push/pull wire extending through the tube, a handle assembly coupled to the push/pull wire and the hollow tube, and a disk segment connected to the push/pull wire and connected to the cylindrical member by a crimp in the cylindrical member. When the handle assembly is actuated, the push/pull wire moves the disk segment and hence the cylindrical member relative to the end effectors and causes the cylindrical member to ride over the arms of the end effectors, thereby forcing the end effectors closed or permitting them to open. Preferably, the disk segment has two curved sides which are coupled to the cylindrical member by crimping, and two substantially parallel sides which provide room for the arms of the end effectors so that the disk segment can move relative to the end effectors. The disk segment also includes a central bore for receiving the push/pull wire.

8 Claims, 14 Drawing Sheets

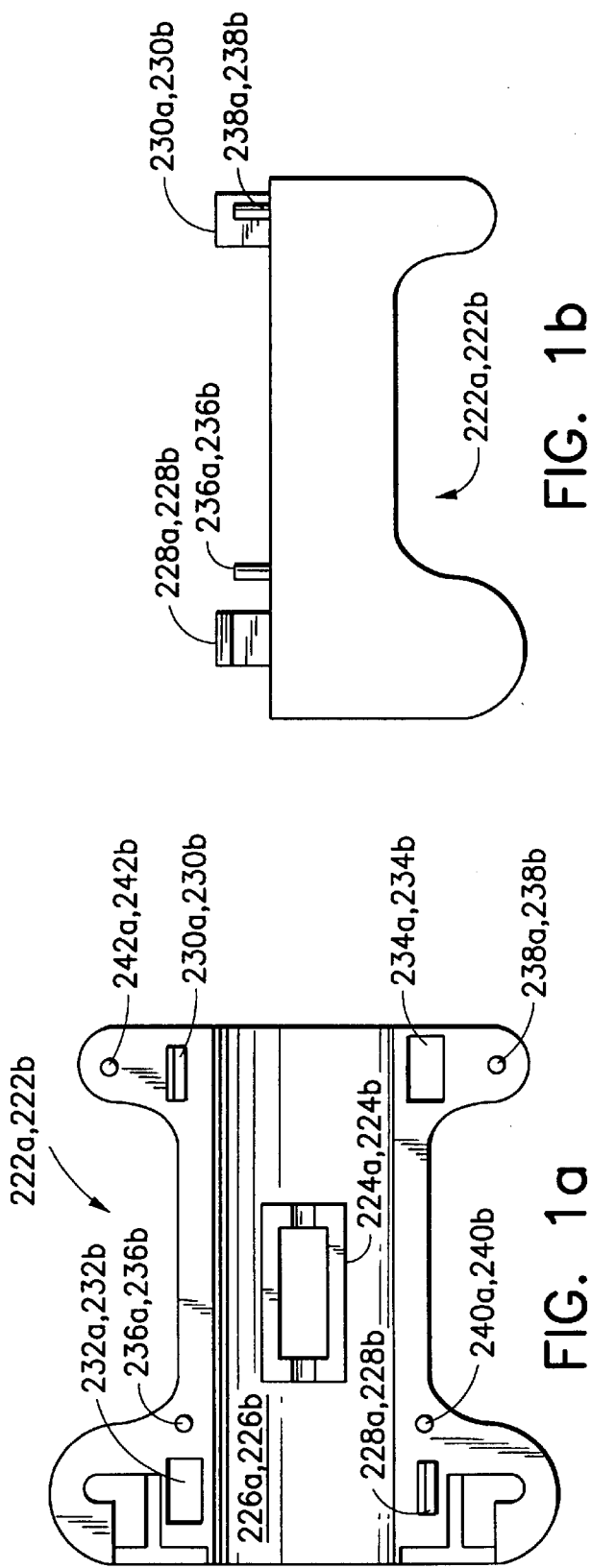
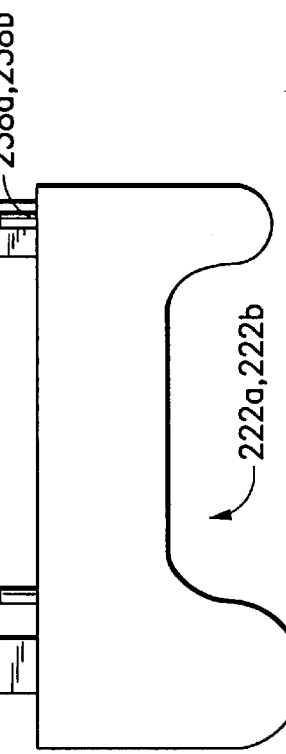
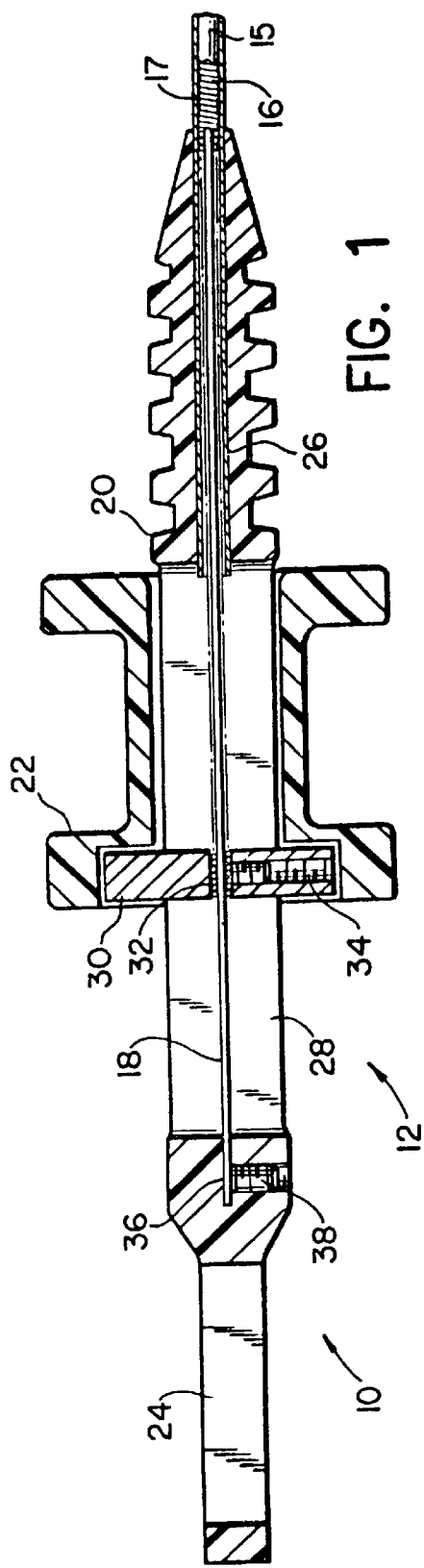

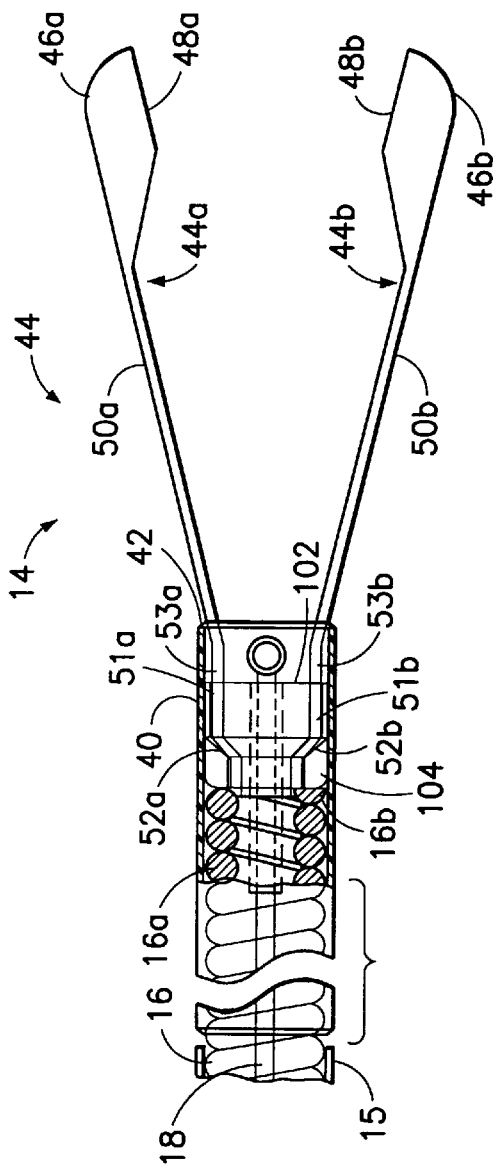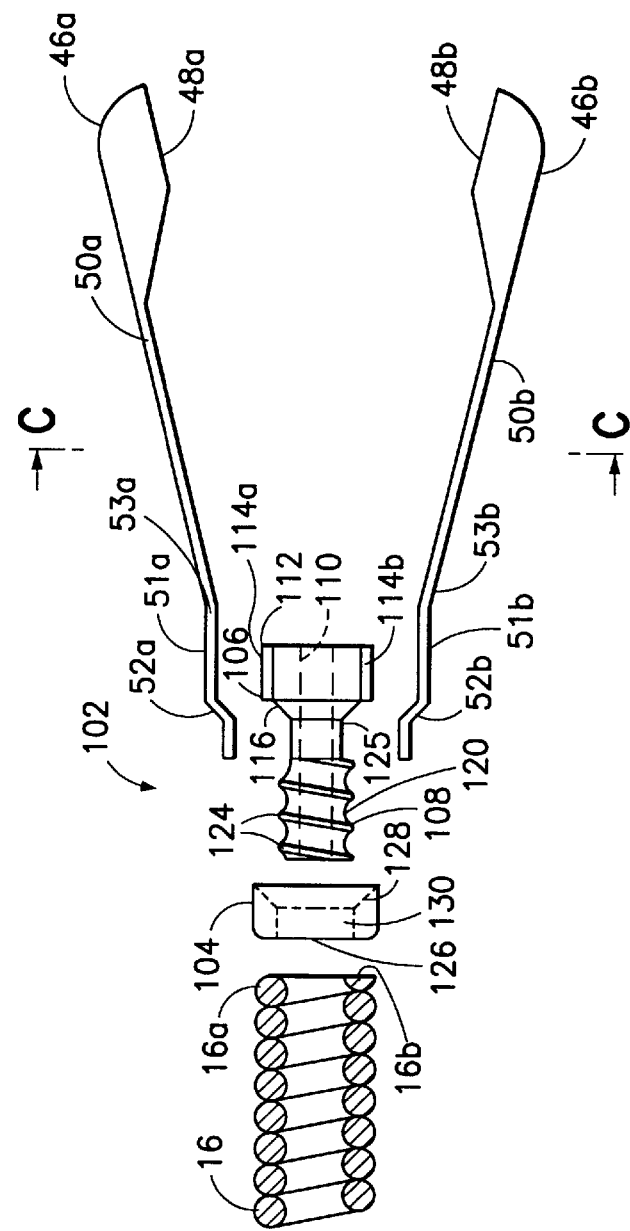
FIG. 2
FIG. 3

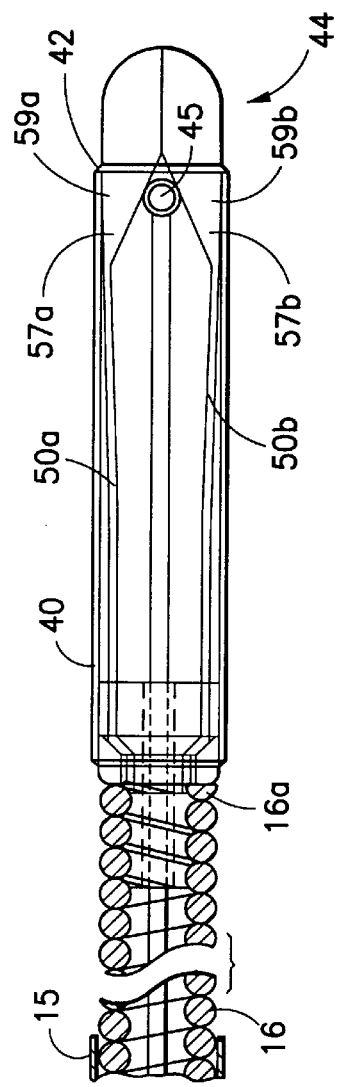
FIG. 5
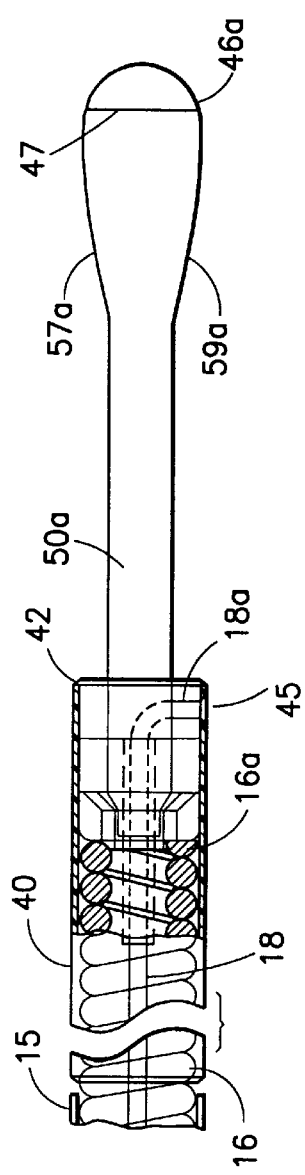
FIG. 6
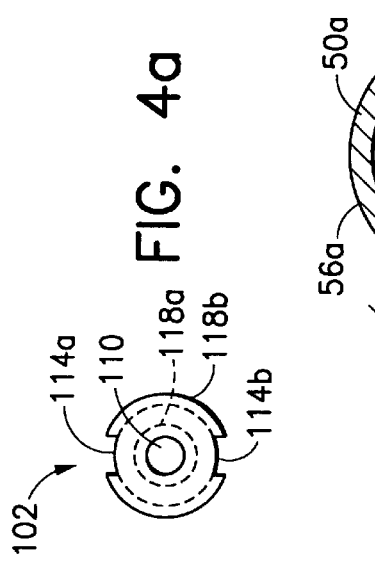
FIG. 4a
FIG. 4c
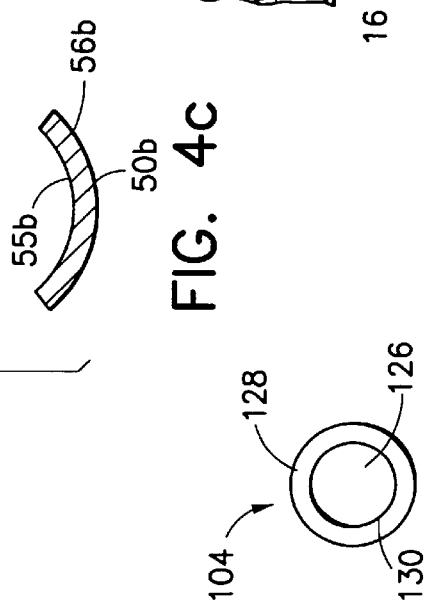
FIG. 4b

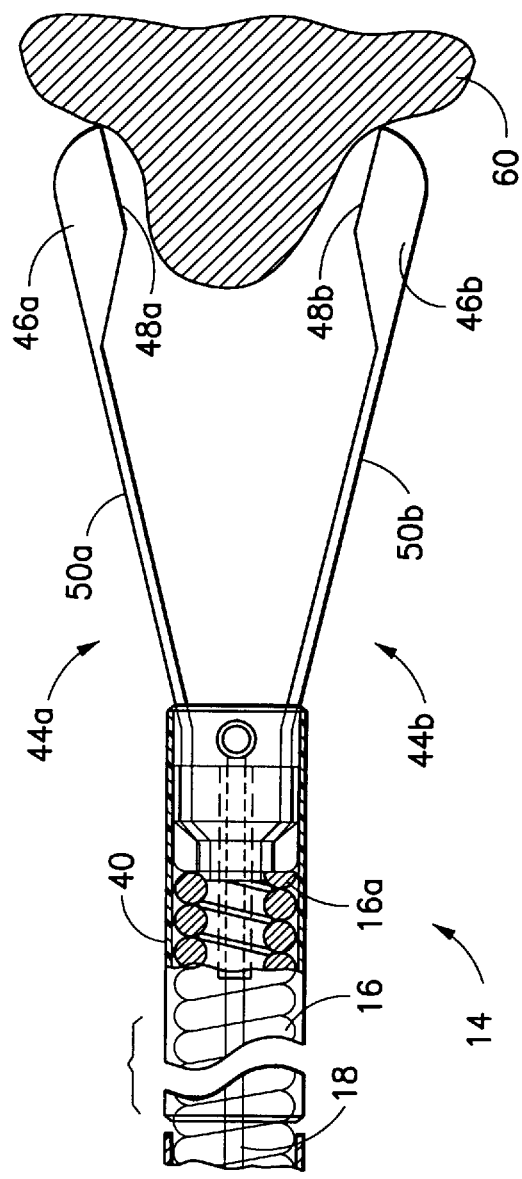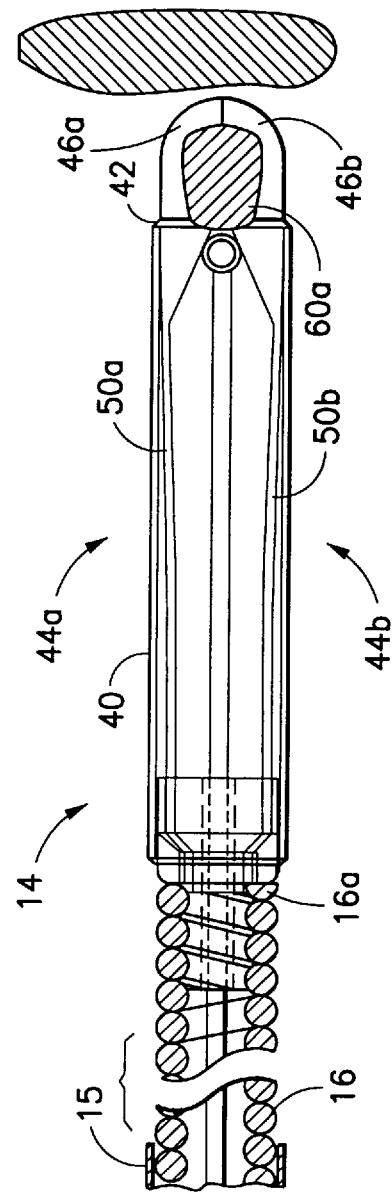
FIG. 7a
FIG. 7b

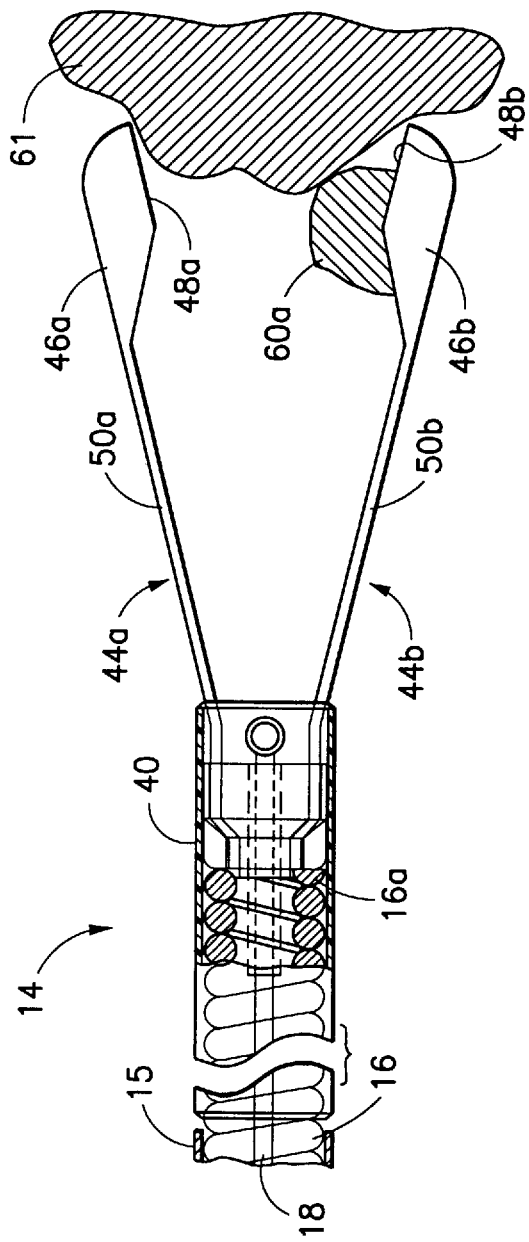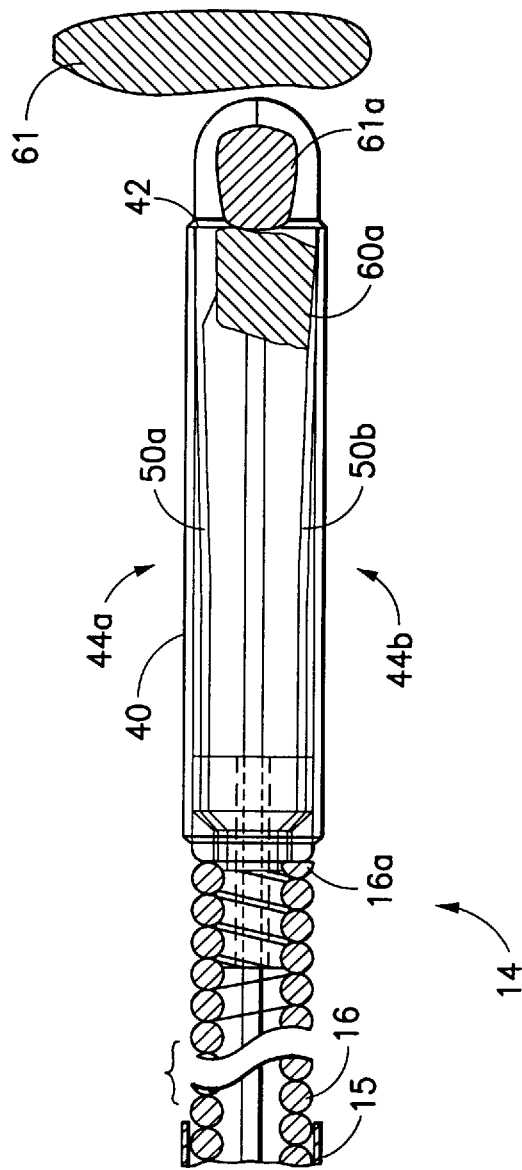
FIG. 7c
FIG. 7d

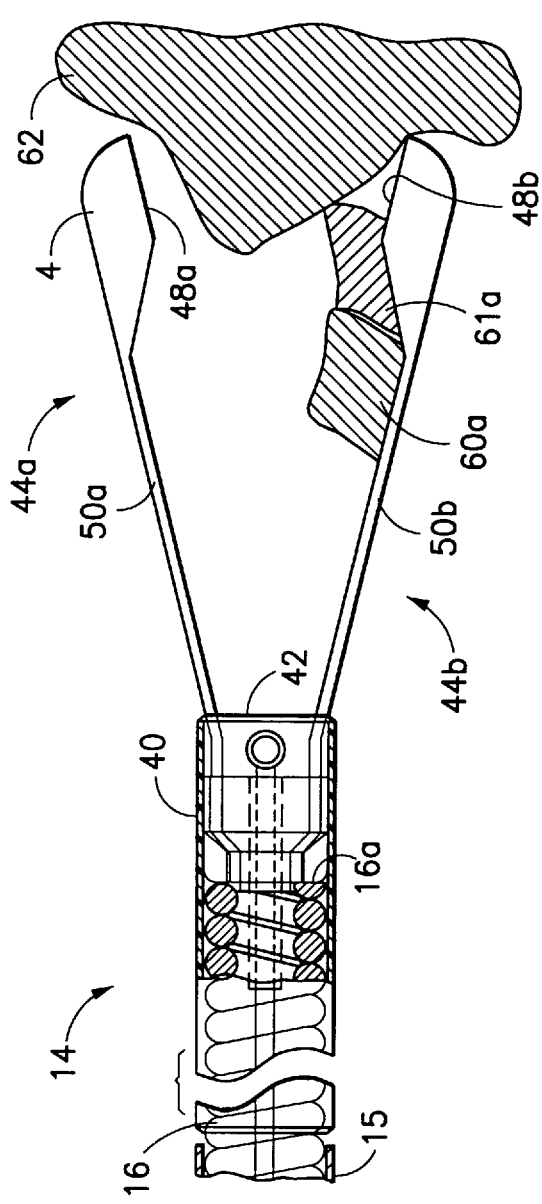
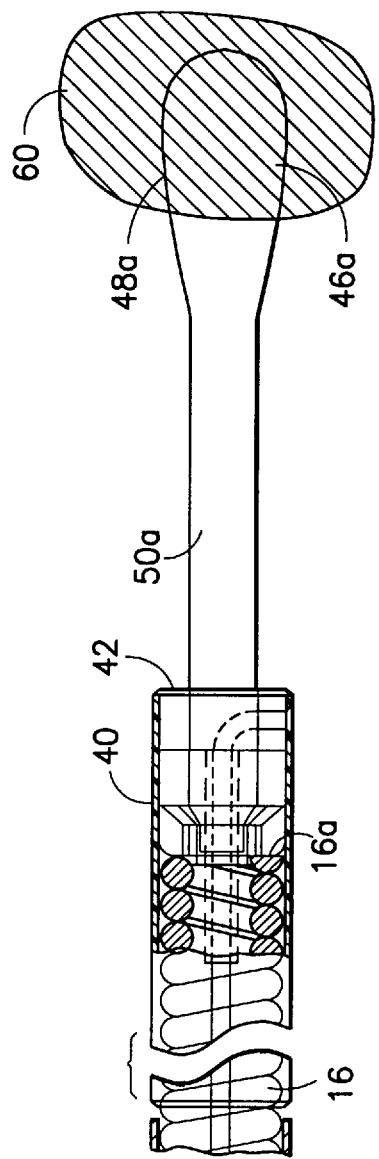
FIG. 7e
FIG. 7f

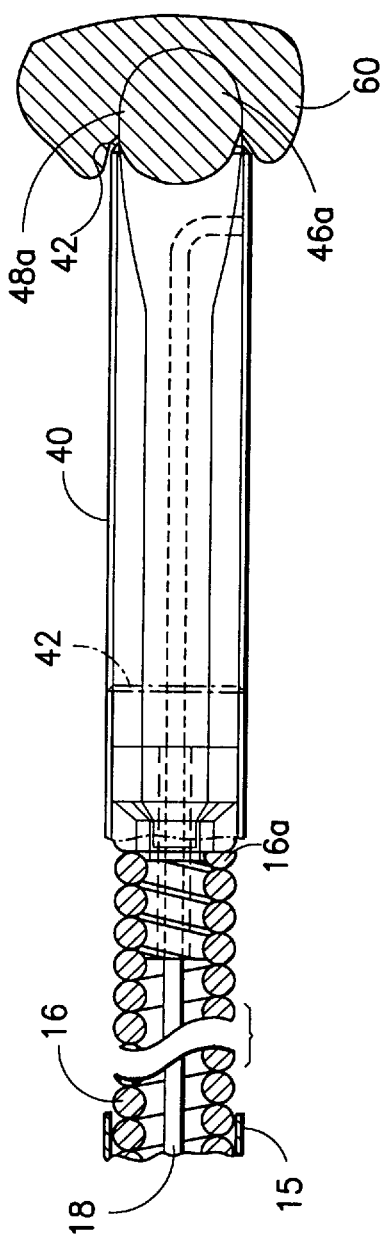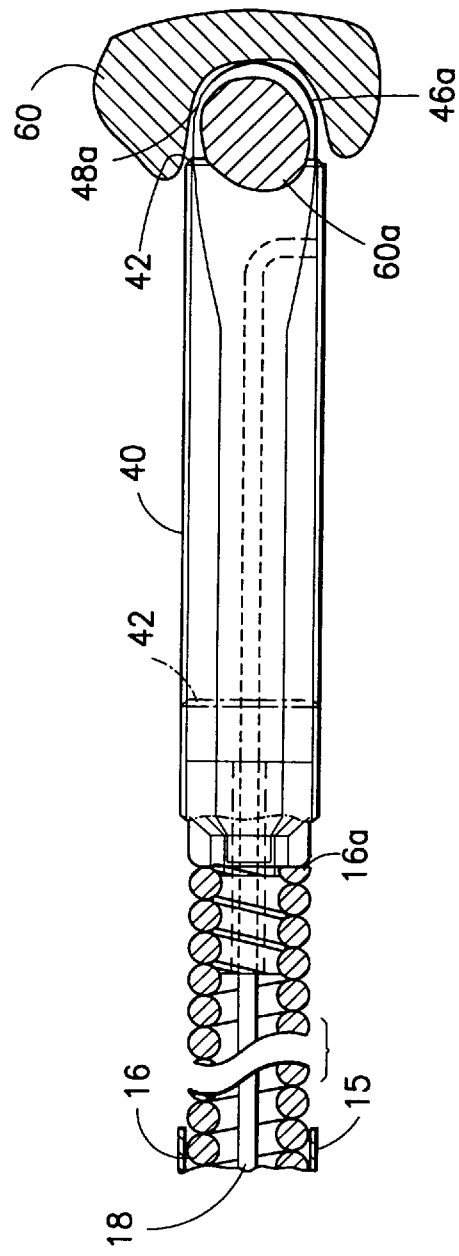

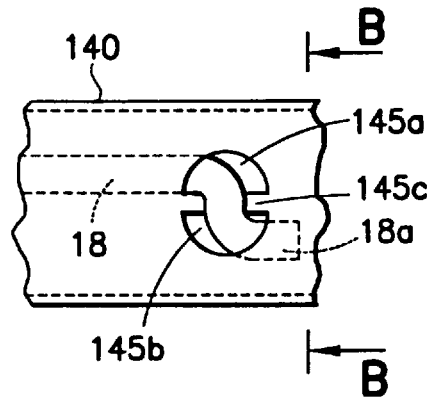
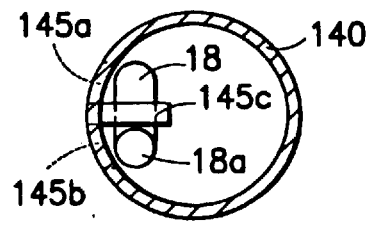
FIG. 8a    FIG. 8b
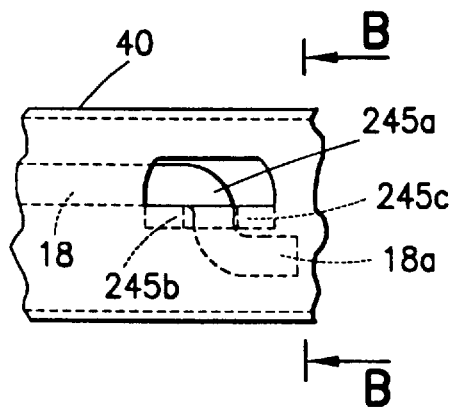
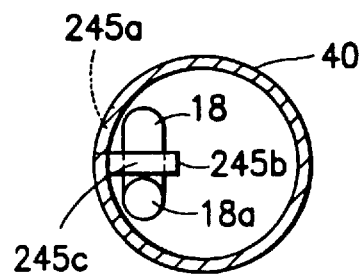
FIG. 9a    FIG. 9b

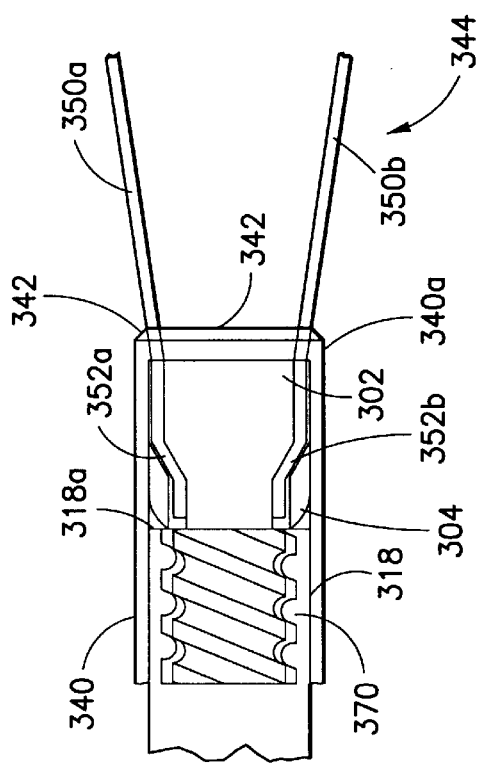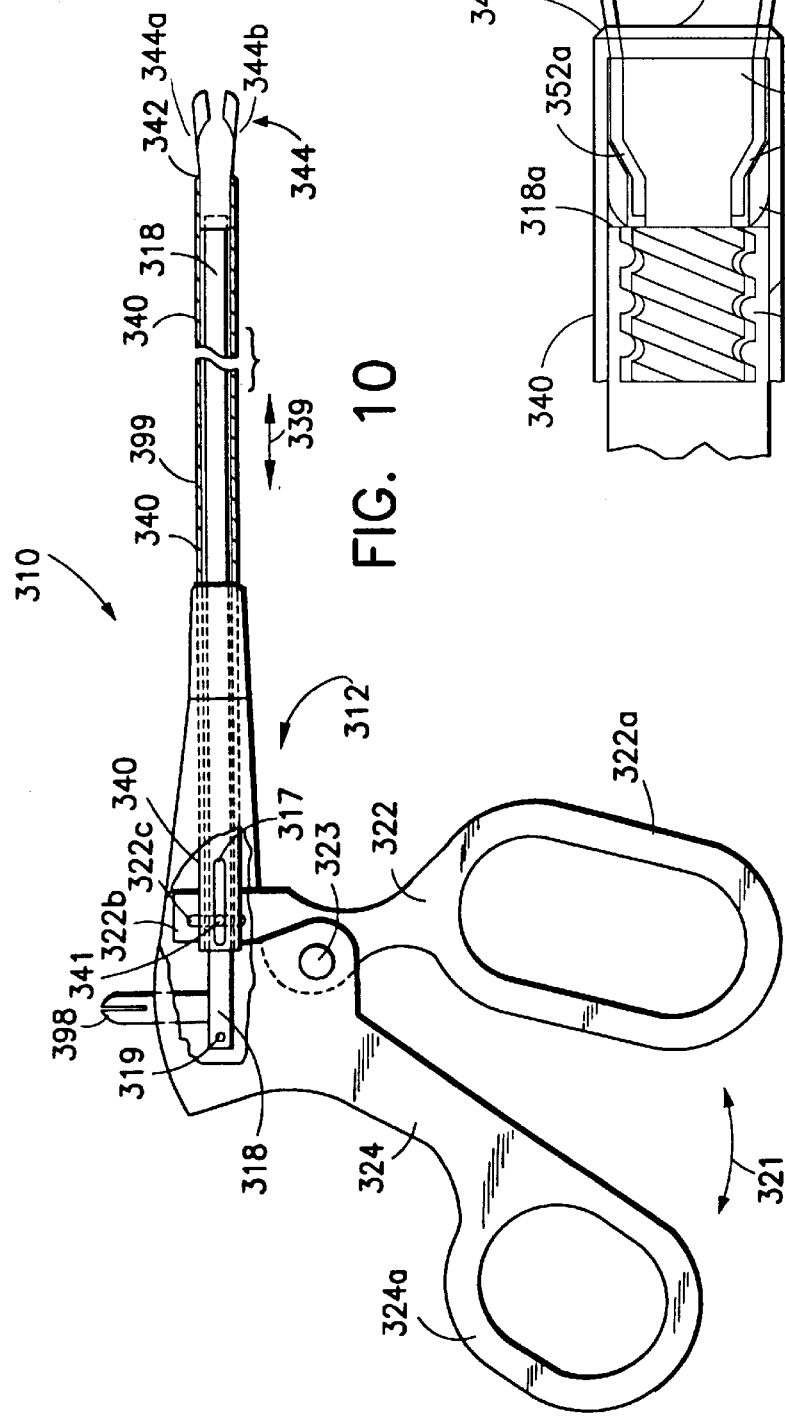

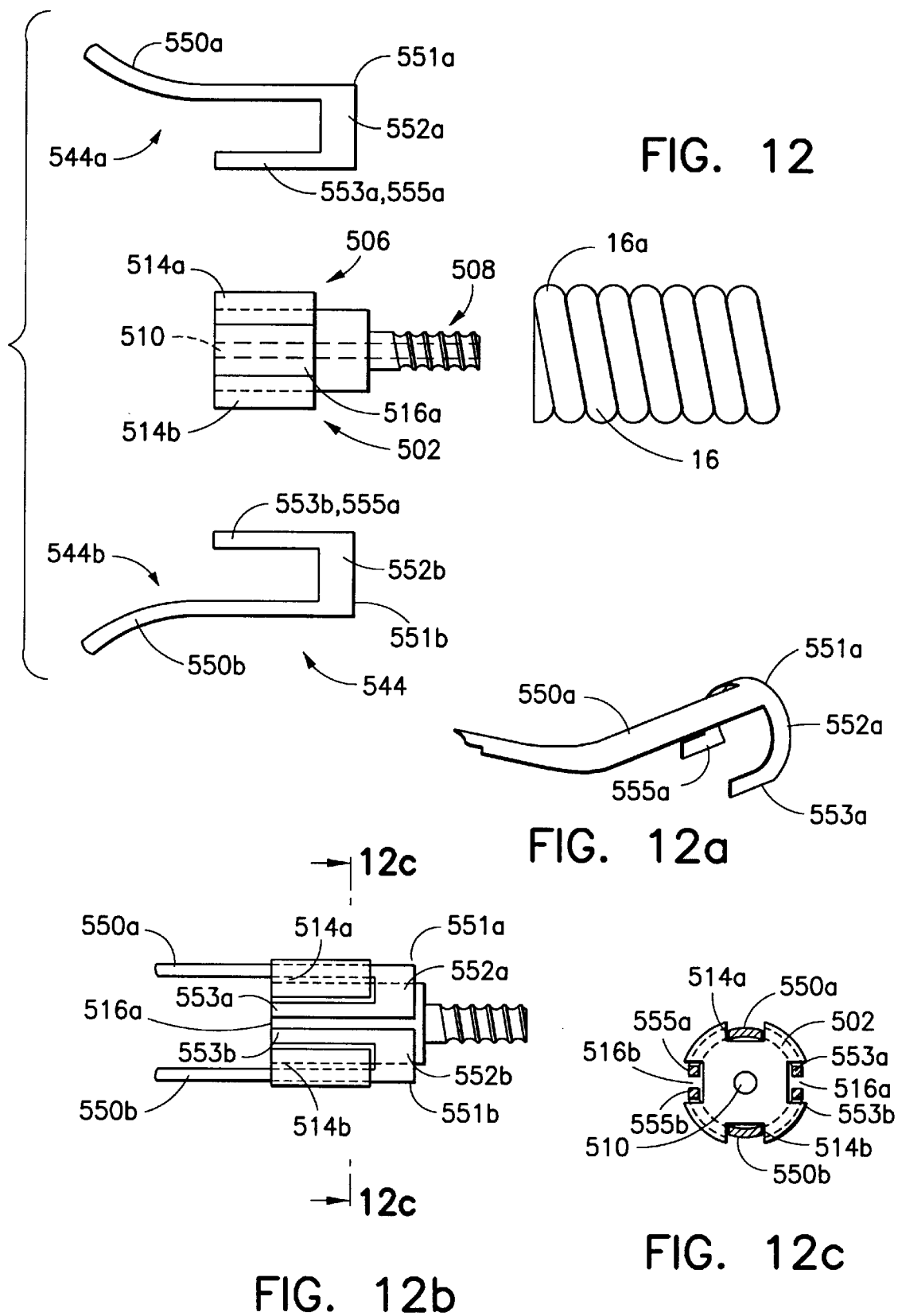

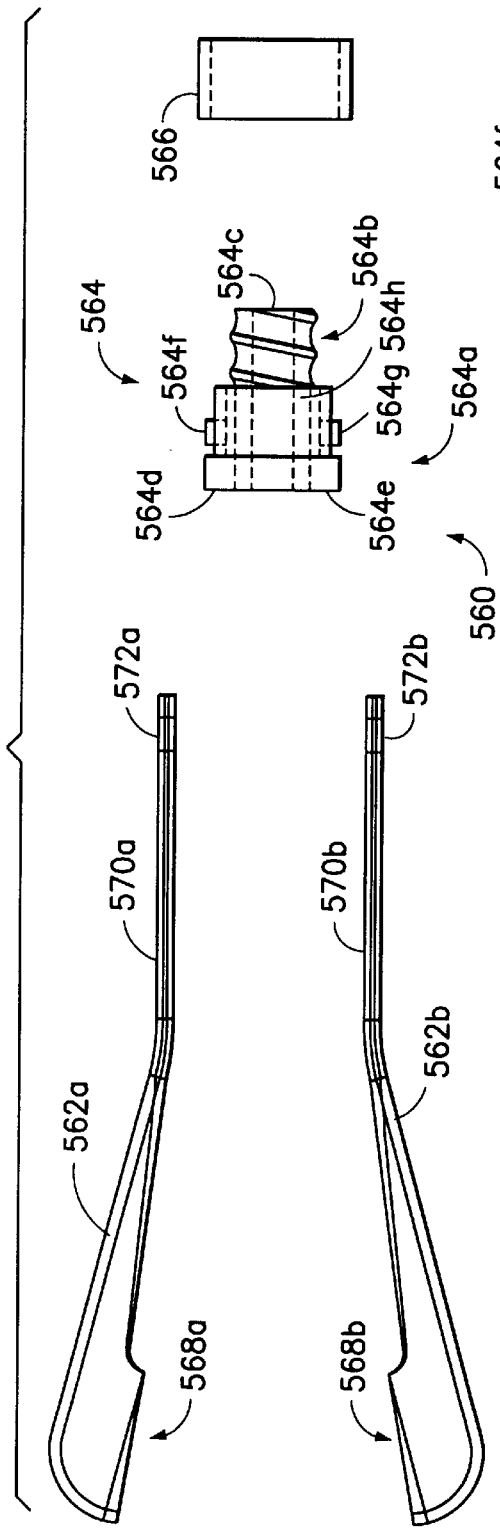
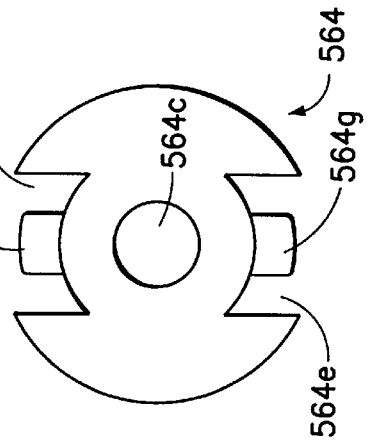
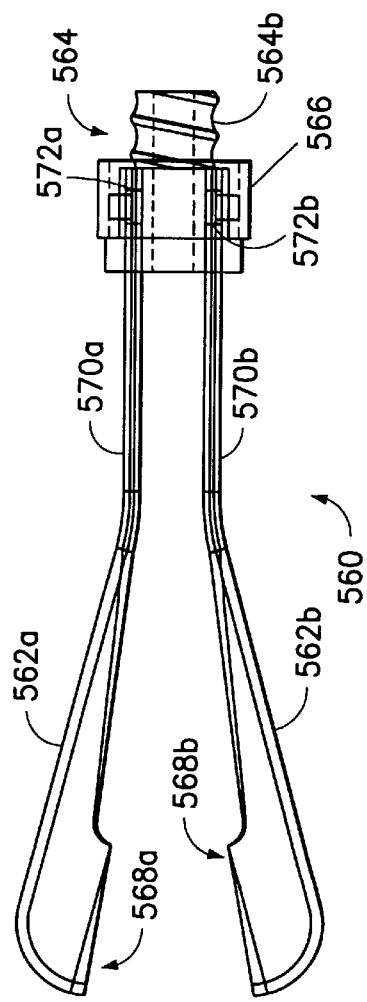

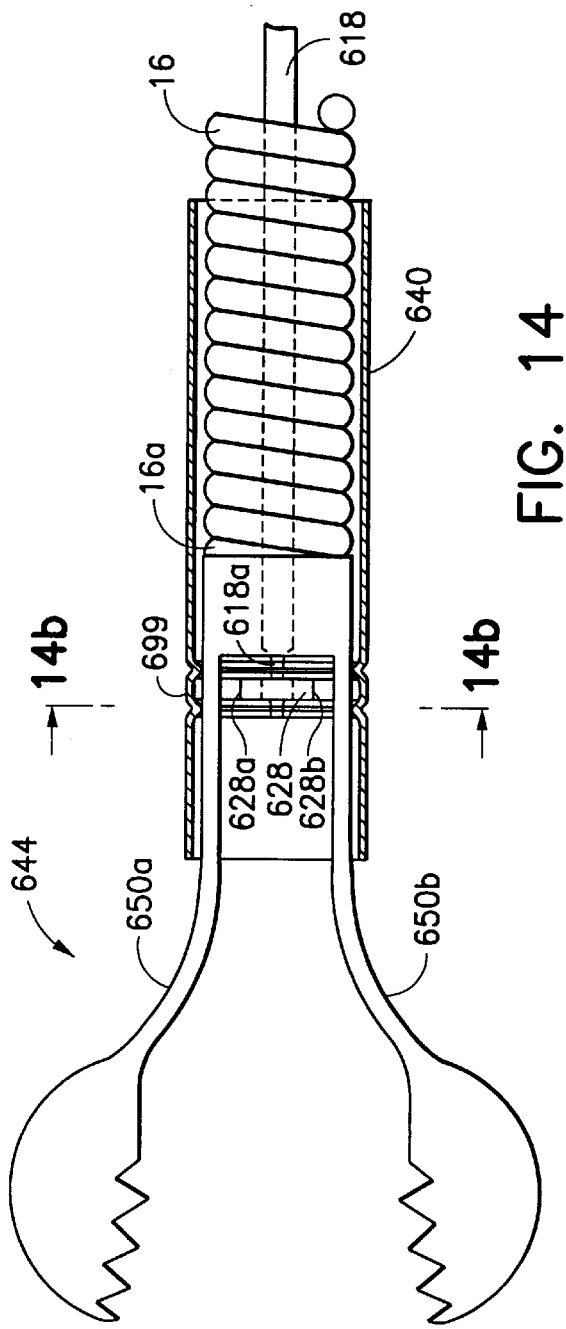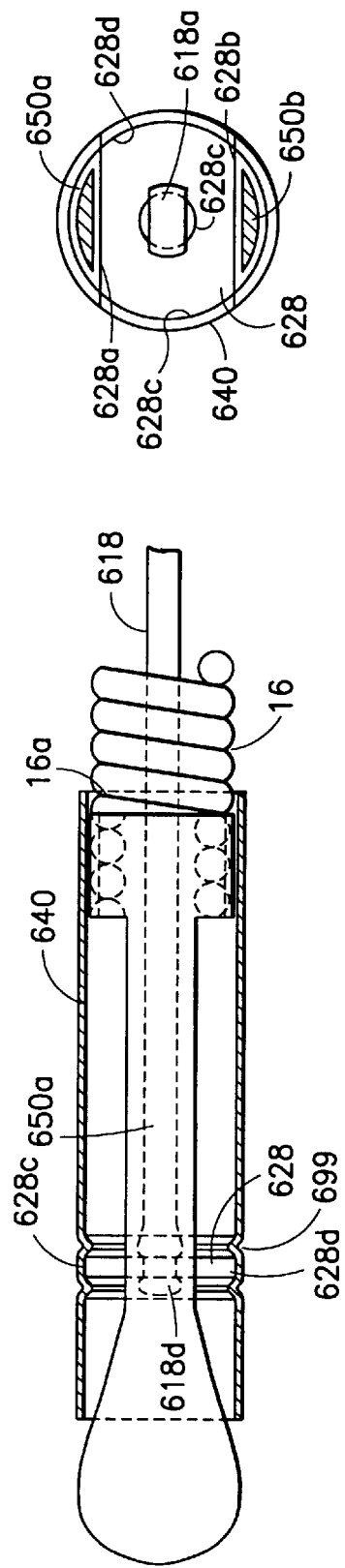

JAW ASSEMBLY FOR AN ENDOSCOPIC INSTRUMENT

This is a continuation of U.S. Ser. No. 08/440,327, filed May 12, 1995, now issued as U.S. Pat. No. 5,507,296, which is a continuation-in-part of U.S. Ser. No. 08/189,937 filed Feb. 1, 1994, now issued as U.S. Pat. No. 5,542,432.

BACKGROUND OF THE INVENTION

1. Field of the Invention

This invention relates to endoscopic surgical instruments. More particularly, this invention relates to super-elastic jaw assemblies for multiple sample endoscopic instruments.

2. State of the Art

Endoscopic biopsy procedures are typically performed with an endoscope and an endoscopic biopsy forceps device (bioptome). The endoscope is a long flexible tube carrying fiber optics and having a narrow lumen through which the bioptome is inserted. The bioptome typically includes a long flexible coil having a pair of opposed jaws at the distal end and manual actuation means at the proximal end. Manipulation of the actuation means opens and closes the jaws. During a biopsy tissue sampling operation, the surgeon guides the endoscope to the biopsy site while viewing the biopsy site through the fiber optics of the endoscope. The bioptome is inserted through the narrow lumen of the endoscope until the opposed jaws arrive at the biopsy site. While viewing the biopsy site through the fiber optics of the endoscope, the surgeon positions the jaws around a tissue to be sampled and manipulates the actuation means so that the jaws close around the tissue. A sample of the tissue is then cut and/or torn away from the biopsy site while it is trapped between the jaws of the bioptome. Keeping the jaws closed, the surgeon withdraws the bioptome from the endoscope and then opens the jaws to collect the biopsy tissue sample.

A biopsy tissue sampling procedure often requires the taking of several tissue samples either from the same or from different biopsy sites. Unfortunately, most bioptomes are limited to taking a single tissue sample, after which the device must be withdrawn from the endoscope and the tissue collected before the device can be used again to take a second tissue sample. The single-sample limitation of most bioptomes is due to the limited space between the biopsy forceps jaws. Several attempts have been made to provide an instrument which will allow the taking of several tissue samples before the instrument must be withdrawn and the samples collected. Problems in providing such an instrument include the extremely small size required by the narrow lumen of the endoscope and the fact that the instrument must be flexible in order to be inserted through the lumen of the endoscope. Thus, several known multiple sample biopsy instruments are precluded from use with an endoscope because of their size and rigidity. These include the "punch and suction type" instruments disclosed in U.S. Pat. No. 3,989,033 to Halpern et al. and No. 4,522,206 to Whipple et al. Both of these devices have a hollow tube with a punch at the distal end and a vacuum source coupled to the proximal end. A tissue sample is cut with the punch and suctioned away from the biopsy site through the hollow tube. It is generally recognized, however, that suctioning tissue samples through a long narrow flexible bioptome is virtually impossible.

Copending application U.S. Ser. No. 08/189,937 discloses an endoscopic multiple sample bioptome which allows for the taking of multiple samples before removal of the bioptome from the endoscope. The multiple sample bioptome includes a hollow outer member and an axially displaceable inner member extending therethrough. The proximal ends of the outer and inner members are coupled to an actuator for axially displacing one relative to the other. The distal end of the outer member is coupled to one of a cylinder having a sharp distal edge and a jaw assembly, while the distal end of the inner member is coupled to the other. The jaw assembly includes a pair of opposed, preferably toothed jaw cups each of which is coupled by a resilient arm to a base member. The arms are bent to urge the jaws away from each other. The base member is mounted inside the cylinder and axial movement of the jaw assembly and cylinder relative to each other draws the arms into the cylinder (or extends the cylinder over the arms) and brings the jaw cups together in a biting action. In this manner, multiple samples from a patient can be taken and stored within the jaw assembly before needing to retrieve the bioptome from the patient.

A family of alloys known to exhibit unusual elasticity and flexibility properties has recently been identified as having useful practical applications. These alloys specifically exhibit what is called the shape memory effect. This effect provides that if such an alloy is plastically deformed from its original shape at one temperature, it will completely recover its original shape on being raised to a higher temperature. In recovering their shapes these alloys can produce a displacement or a force, or a combination, as a function of the temperature. Due to the unique atomic structure necessary for the memory shape effect to take place, these alloys exhibit other properties as well, such as super-elasticity or pseudo-elasticity.

The type of transformation which occurs in the shape memory alloys is known as a martensitic transformation and changes the material from a high temperature form, called austenite, to a low temperature form called martensite. For a given shape memory alloy, the transformation between martensite form and austenite form occurs at a predictable temperature, known as the transformation temperature.

In order for an alloy to exhibit the shape-memory effect, it must first be bent into the shape to be "memorized" at room temperature. The alloy is then heated until it assumes a high-temperature configuration called the beta or parent phase, where the crystal structure of the metal assumes its austenite form which it will "remember". Next, the alloy is rapidly cooled so that the atoms in the alloy rearrange themselves into the crystal form of martensite. The alloy may then be bent into a new shape which it will maintain as long as the temperature remains below the transformation temperature. If the alloy is subsequently reheated above its transformation temperature so that the alloy molecular structure reverts to an austenite form, it will recover its previously memorized shape. Shape memory alloys exhibit significantly increased resiliency relative to their non-superelastic counterparts, because the atoms of the memory metal shift back and forth between martensite and austenite forms, and do not slip into new dislocated configurations as is the case with normal metals.

Useful temperature independent properties are also exhibited by memory-shape alloys. In an alloy that has a beta phase capable of producing martensite under stress, one can observe an unusual elastic property called super-elasticity or pseudo-elasticity. In a typical alloy with this property, the metal exhibits normal elastic behavior under stress (that is, it gets longer in some dimensions) until the critical stress is reached at which point martensite molecular structures begin to form. With further stress, the specimen continues to elongate, as if it were being plastically deformed. When the stress is removed, the martensite structure reverts to the parent phase, or austenite structure, and the metal contracts to its original dimensions, showing no permanent deformation.

Presently, the applications of shape memory materials in medical apparatuses are very limited. U.S. Pat. No. 4,925,445 to Sakamoto et al. discloses a guide wire for a catheter, where the guide wire has a rigid body and a flexible distal end made of a memory-shape metal alloy with the super-elastic properties described above. The distal end of the wire is curved back such that a blunt forward tip is formed. With a super-elastic distal end, the guide wire can be guided through the blood vessel of a patient without the risk of permanently deforming the tip of the wire, which could result in the tearing of the blood vessel walls or in the misguiding of the wire. U.S. Pat. No. 5,254,130 to Poncet et al., similarly uses a memory-shaped alloy as a push rod and steering means for steering a distal clevis and attached end effectors. As the push rod is extended outside of the housing where it is held prior to deployment, the push rod assumes a remembered configuration relative to the straight housing, and hence steers the end effectors to a desired position. Other than the steering functions disclosed in the Sakamoto et al. and Poncet et al. patents, however, the super-elasticity of shape memory alloys has not been used in medical apparatus of the art.

SUMMARY OF THE INVENTION

It is therefore an object of the invention to provide a jaw assembly for a bioptome where at least portions of the jaw assembly are made out of a superelastic metal.

It is another object of the invention to provide a jaw assembly for an endoscopic multiple sample bioptome where the jaw arms are superelastic and flexible and repeatedly return to desired positions without fracturing or deforming.

It is a further object of the invention to provide a jaw assembly for an endoscopic multiple sample bioptome where the arms of the jaw assembly undergo insignificant plastic deformation even after repeatedly being opened and forced closed.

It is also an object of the invention to provide a jaw assembly for an endoscopic multiple sample bioptome which is simple to assemble.

In accord with these objects which will be discussed in detail below, an endoscopic bioptome is provided with a jaw assembly, a tubular member, and an axially displaceable wire extending through the tube member, where the distal end of the wire and tubular member are both coupled to the jaw assembly, and the jaw assembly includes a pair of opposed end effectors having resilient arms formed from a superelastic metal. According to a first embodiment of the invention, the proximal ends of the resilient arms include angled portions, while the distal ends terminate with end effector jaw cups, which are also preferably formed from a superelastic metal. The resilient arms urge the jaw cups away from each other. As the resilient arms are formed from a superelastic alloy, they exhibit very high resiliency and durability even after numerous uses. Other embodiments of the jaw assembly include arms having mounting holes and cups having radially arranged teeth and closing cams. Another embodiment of the jaw assembly includes arms having proximal semi-cylindrical portions with distally extending tabs. Different types of mounting screws are provided for coupling the proximal ends of the arms of the jaws to the distal end of the tubular member.

According to preferred aspects of the invention, the tubular member is a flexible coil, and the proximal portion of each arm is mounted inside the distal end of the tubular member by means of a threaded screw and washer (or retaining sleeve) threaded in the coil. The distal end of the wire is coupled to a cylinder which is preferably provided with a knife sharp distal edge. Different embodiments for coupling the distal end of the wire to the cylinder are disclosed. The proximal ends of the coil and wire are coupled to a manual actuation means for axially displacing one of the coil and wire relative to the other. Axial movement of the wire relative to the coil moves the cylinder over the arms of the end effectors and over the necks of the jaw cups, thereby forcing the jaw cups together in a biting action.

According to another embodiment of the invention, a laparoscopic type multiple sample bioptome is provided with the super-elastic jaw assembly of the invention. The laparoscopic type bioptome is provided with a relatively rigid hollow tube, and a relatively rigid rod which extends therethrough. The distal end of the rod is coupled to the jaw assembly described in the first embodiment, and the distal end of the tube is provided with a knife-sharp edge similar to the cylinder edge described above. The proximal end of the rod is coupled to a fixed portion of a handle and the proximal end of the tube is coupled to a movable lever portion of the handle. Movement of the lever of the handle results in longitudinal movement of the tube relative to the rod and effects and closing of the jaws as described above.

Additional objects and advantages of the invention will become apparent to those skilled in the art upon reference to the detailed description taken in conjunction with the provided figures.

BRIEF DESCRIPTION OF THE DRAWINGS

FIG. 1 is a side elevation view in partial section of the proximal end of a first embodiment of the invention;

FIG. 1a is a plan view of one hermaphroditic part of a two part spool according to a preferred embodiment of the invention;

FIG. 1b is a side elevation view of the one part of the two part spool;

FIG. 2 is an enlarged transparent side elevation view of the distal end of a first embodiment of the invention with the jaws open;

FIG. 3 is an enlarged exploded side view of the distal end of a first embodiment of the invention;

FIGS. 4a and 4b are respectively a front view of the threaded screw and a front view of the washer of FIG. 3;

FIG. 4c is a cross sectional view taken along line C—C of the arms of the jaw assembly shown in FIG. 3;

FIG. 5 is an enlarged transparent side elevation view of the distal end of a first embodiment of the invention with the jaws closed;

FIG. 6 is an enlarged transparent top elevation view of the distal end of a first embodiment of the invention;

FIGS. 7a through 7e are enlarged transparent side elevational views of the distal end of the first embodiment, showing a sequence of biopsy sampling operations;

FIGS. 7f through 7h are views similar to FIG. 6 showing the cutting action of the knife-sharp distal edge of the cylinder;

FIG. 8a is an enlarged broken side elevation view of a different embodiment of control wire coupling;

FIG. 8b is a cross sectional view along line B—B in FIG. 10a;

FIG. 9a is a view similar to FIG. 8a but of yet another embodiment of control wire coupling;

FIG. 9b is a cross sectional view along line B—B of FIG. 9a;

FIG. 10 is a broken side elevation view in partial section of a second embodiment of the invention;

FIG. 10a is an enlarged transparent side elevation view of the jaw assembly to push rod and outer tube coupling of the second embodiment of the invention of FIG. 10 with the jaws open;

FIG. 12 is an enlarged exploded side elevation view of another embodiment for mounting jaws on the distal end of a coil;

FIG. 12a is a broken perspective view of a jaw arm according to the embodiment of FIG. 12;

FIG. 12b is broken side elevation view of the embodiment of FIG. 12 in a partially assembled state;

FIG. 12c is a sectional view taken along line 12c—12c in FIG. 12b;

FIG. 13 is an exploded side elevation view of a presently preferred embodiment for mounting jaws on the distal end of a coil;

FIG. 13a is an enlarged distal end view of the screw in FIG. 13;

FIG. 13b is a reduced, partially transparent, side elevation view of the embodiment of FIG. 13 as assembled prior to attachment to the distal end of a coil;

FIG. 14 is an enlarged side elevation view of another embodiment for coupling a cylindrical sleeve to the distal end of a control wire;

FIG. 14a is a top view of the embodiment of FIG. 13; and

FIG. 14b is an enlarged sectional view taken along lines 13b—13b of FIG. 13.

DETAILED DESCRIPTION OF THE PREFERRED EMBODIMENTS

Figure 1C:
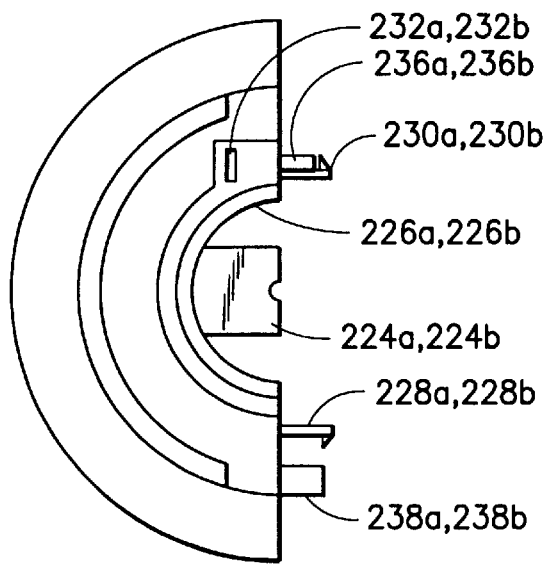
FIG. 1c proximal end view of the one part of the two part spool.
Figure 1D:
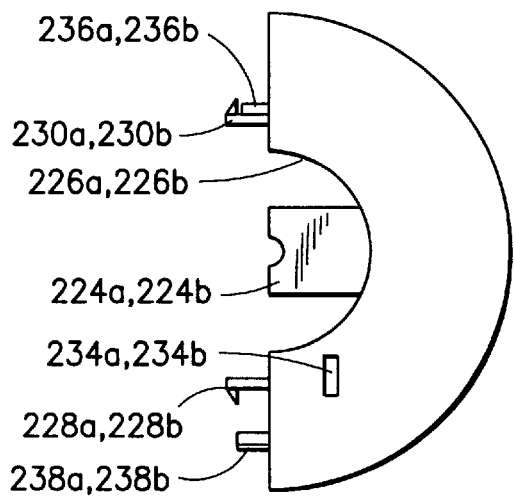
FIG. 1d is a distal end view of the one part of the two part spool.

Referring now to FIGS. 1 through 6, a first embodiment of the multiple sample bioptome with the super-elastic flexible jaw assembly is shown and includes a proximal handle portion 12 and a distal end effector portion 14. A long flexible coil 16, and an axially displaceable control wire 18 which extends through the coil 16 couples the handle portion 12 to the end effector portion 14. The coil 16 is preferably covered with a PTFE, FEP or polyolefin sheath 15 along substantially all of its length and a strain relief sleeve 17 covering a portion of the coil which extends from the handle 12. The coil 16, by its nature is effectively internally threaded and can receive a screw with mating threads, as discussed in further detail below, at its open distal end 16a which is preferably ground flat 16b. The control wire 18 is preferably flexible but longitudinally inelastic and is ideally formed from 304 Steel and provided with an outer diameter of approximately 0.017–0.018 inch. The proximal handle portion 12 includes a central shaft 20 and a displaceable spool 22. The proximal end of the shaft 20 is provided with a thumb ring 24 and a longitudinal bore 26 is provided at the distal end of the shaft 20. A longitudinal slot 28 extends from the proximal end of bore 26 to a point distal of the thumb ring 24. The displaceable spool 22 is provided with a cross member 30 which passes through the slot 28 in the central shaft 20. The cross member 30 is provided with a central through hole 32 and a radially engaging set screw 34. According to the first embodiment of the invention, a short bore 36 and a radially engaging set screw 38 are provided in the shaft 20 distal of the thumb ring 24 with the bore 36 communicating with the longitudinal slot 28. In the first embodiment of the invention, the proximal end of the coil 16 extends into the central through hole 32 in the cross member 30 and is fixed there by the set screw 34. The proximal end of the control wire 18, passes through slot 28, is inserted into the short bore 36, and held there by the set screw 38. From the foregoing, those skilled in the art will appreciate that relative movement of the shaft 20 and spool 22 results in movement of the control wire 18 relative to the coil 16. Such action results in actuation of the end effectors as described in detail below.

According to a preferred embodiment of the invention, an hermaphroditic two part snap-together spool is used. FIGS. 1a through 1e illustrate the principal features of each part 222a (222b) of a snap together spool. Two identical hermaphroditic parts 222a (222b) each represent one half of the spool. Each part 222a (222b) is substantially semi-cylindrical with a spool shaped outer profile. A coil engaging member 224a (224b) extends radially inward within a semi-cylindrical recess 226a (226b) which extends the entire length of the part 222a (222b). Each part 222a (222b) is provided with a pair of diametrically opposed locking tabs 228a (228b), 230a (230b) and a pair of diametrically opposed tab receiving slots 232a (232b), 234a (234b). In addition, each part 222a (222b) is provided with a pair of diametrically opposed guide pins 236a (236b), 238a (238b) and a pair of diametrically opposed pin receiving holes 240a (240b), 242a (242b). From the foregoing, it will be appreciated that when the two parts 222a, 222b are assembled, the guide pins 236a, 238a on part 222a enter the pin receiving holes 240b, 242b, respectively, on part 222b; and the locking tabs 228a, 230a on part 222a enter the tab receiving slots 232b, 234b, respectively, on part 222b. Similarly, the guide pins 236b, 238b on part 222b enter the pin receiving holes 240a, 242a, respectively, on part 222a; and the locking tabs 228b, 230b on part 222b enter the tab receiving slots 232a, 234a, respectively, on part 222a. Prior to the snapping the parts together, the proximal end of the coil 16 (FIG. 1) with a crimp band (not shown) on its end is placed between the coil engaging members 224a, 224b. When the parts 222a, 222b are assembled the respective coil engaging members 224a, 224b hold the proximal end of the coil securely.

Figure 1E:
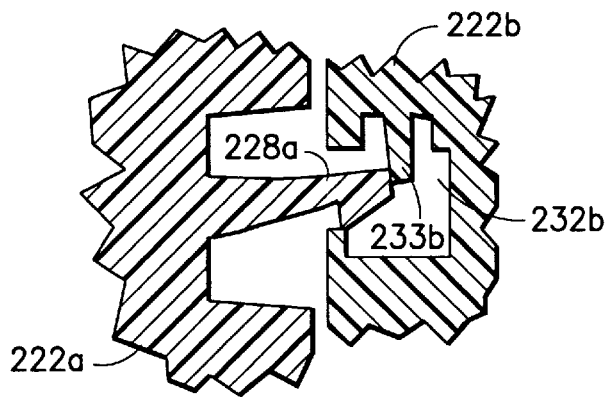
FIG. 1e is a broken schematic section illustrating a leaf spring locking of two parts of the two part spool.

According to a preferred aspect of the two part spool, the tab receiving slots are provided with leaf springs to inhibit the two parts from coming apart. FIG. 1e illustrates the leaf spring schematically with reference to the tab 228a on part 222a as it engages the slot 232b on part 222b. As seen in FIG. 1e, the slot 232b is partially occluded by a depending arm 233b which acts like a leaf spring when it is engaged by the tab 228a as it enters the slot 232b. After the tab 228a enters the slot 232b, the arm 233b will prevent the tab 228a from rising out of the slot 232b.

Turning now to FIGS. 2 through 6, the end effector portion 14 includes a cylindrical sleeve 40, preferably having a knife-sharp distal edge 42, and a jaw assembly 44. The jaw assembly 44 includes a pair of end effectors 44a, 44b, a screw 102, and a washer or retaining sleeve 104. Each end effector 44a, 44b includes a jaw cup 46a, 46b preferably having a knife-sharp rim 48a, 48b (or radially arranged teeth as described in detail below), and a resilient, preferably narrow, arm 50a, 50b which extends proximally from the jaw cup 46a, 46b. The narrow arm 50a, 50b, at its proximal end 51a, 51b, preferably includes a sharply descending angled portion 52a, 52b, and a gently angled portion 53a, 53b. At least the gently angled portion 53a, 53b of the arms 50a, 50b, and preferably the entire arms 50a, 50b are formed from super-elastic memory metal such as Nitinol (a nickel-titanium alloy), and are biased apart from each other (due to angled portions 53a, 53b of the arms 50a, 50b), thereby urging the jaw cups 46a, 46b apart (as seen in FIG. 2). In addition, as the arms 50a, 50b and the jaws 46a, 46b are preferably integral with each other, the jaws are preferably formed from a super-elastic or shape metal. However, it should be appreciated that while it is preferable to form the entire arm and jaw from a super-elastic or shape memory metal, the jaw cups 46a, 46b and proximal ends 51a–b, 51a–b of the jaws 44 may be made of any other material and attached to the resilient arms 50a, 50b by any conventional and appropriate means.

According to the first embodiment of the invention, the proximal end 51a, 51b of each arm 50a, 50b is coupled to the distal end 16a of the coil 16 by crimping/locking with a hollow threaded screw 102 and a washer 104 as best illustrated in FIGS. 3 and 4. The threaded screw 102 is substantially cylindrical, and generally includes a head portion 106, a threaded portion 108, and a cylindrical through-bore 110 along its central axis. The throughbore 110 is dimensioned to receive and allow lateral movement of the control wire 18. The distal end 112 of the head portion 106 has a diameter substantially equal to that of the outer diameter of the coil 16, and is provided with two opposing grooves 114a, 114b (see FIG. 4a) on the outer perimeter of the distal end 112 of the head portion 106. Grooves 114a, 114b are dimensioned to receive the angled portion 52a, 52b at the proximal end 51a, 51b of each of the narrow arms 50a, 50b. The proximal end 116 of the head portion 106 is shaped as a truncated cone (i.e., frustroconical) and has a larger diameter 118b at the distal end 112 of the head portion 106 and a smaller diameter 118a at the distal end 120 of the threaded portion 108. The threaded portion 108 has a diameter substantially equal to the inner diameter of the coil 16 and the proximal end 122 of the threaded portion 108 includes threads 124 for lockingly engaging the interior of the distal end 16a of the coil 16.

The washer 104 is substantially cylindrical, and generally includes a throughbore 126 having proximal 128 and distal 130 sections. The distal section 128 of the throughbore 126 is shaped as a truncated cone, and the proximal section 130 extends therefrom. It will be appreciated that the throughbore 126 of the washer 104 has substantially the same configuration as the proximal end 116 of the head portion 106 of the screw 102 and distal end 120 of the threaded portion 108 of the screw 102. It will now be understood that the throughbore 126 of the washer 104 is dimensioned for engaging the proximal end 116 of the head portion 106 of the screw 102 and distal end 125 of the threaded portion 108 of the screw 102 when the stepped 52a, 52b proximal ends 51a, 51b of the narrow arms 50a, 50b are positioned about the grooves 114a–b of the threaded screw 102 as described above. The proximal end 120 of the threaded portion 108 of the threaded screw 102 is then threaded into the interior of the distal end 16a of the coil 16. As can be seen in FIGS. 2 and 3, the washer 104 is fastened between the head portion 106 of the threaded screw 102 and the distal end 16a of the coil 16. The stepped 52a, 52b proximal ends 51a, 51b of the narrow arms 50a, 50b are thus fastened between the washer 104 and the threaded screw 102.

As can be seen in FIG. 4c, the preferred end effector arms 50a, 50b have a substantially arced shape in cross section with inner and outer curved walls 55a, 55b, 56a, 56b. It will be appreciated that the arced shape of the arms extends the length of the narrow arms from the jaws 44a, 44b, back to the angled proximal portions 52a, 52b. With this arrangement, the tube 40 will slide easily over the arms as will be described hereinafter. In addition, the angled proximal portions 52a, 52b of the jaws 44a, 44b matingly engage the grooves 114a, 114b (see FIG. 4a) on the outer perimeter of the distal end 112 of the threaded screw 102 head portion 106.

Referring to FIGS. 2, 5 and 6, it will be seen that the cylindrical sleeve 40 is coupled to the distal end of the control wire 18 by providing the sleeve 40 with a lateral hole 45 which engages a bent end 18a of the control wire 18. As illustrated, the bent end 18a of the control wire 18 is welded to the hole 45 in the side of the sleeve 40. However, as will be described in detail hereinbelow, other methods of coupling the control wire to the sleeve are possible. The cylindrical sleeve 40 is slidably mounted over the cylindrical washer 104 and head portion 106 of the threaded screw 102, and is axially movable over the arced resilient arms 50a, 50b, thereby bending the arms at the gently bent locations 53a, 53b, and closing the jaws 46a, 46b as shown in FIG. 5. As the resilient arms 50a, 50b are made of superelastic metal, they will immediately return to their original open position (FIG. 2) once the cylinder sleeve 40 is retracted. Furthermore, even after repeatedly sliding the cylinder sleeve 40 back and forth over the arms 50a, 50b, the jaw assembly 44 will maintain its original shape due to the above described properties of the superelastic metal.

As seen in FIG. 6, the jaw cups 46a, 46b have an eccentric, albeit symmetrical outline with their widest point indicated by the line 47. Distal of the line 47, the jaw cups are substantially hemispherical and proximal of the line 47, the jaw cups are substantially hemi-elliptical. The jaw cups are arranged so that the rims are substantially aligned when closed as shown in FIG. 5. It will also be seen from FIGS. 5 and 6 that the side walls 57, 57b, 59a, 59b of the jaw cups 46a, 46b taper towards the arms 50a, 50b to provide a smooth transition from the jaw cups to the arms.

From the foregoing description and with reference to FIGS. 1 through 6, those skilled in the art will appreciate that when the spool 22 and the shaft 20 are axially displaced relative to each other, the cylindrical sleeve 40 and the end effectors 44a, 44b are similarly axially displaced relative to each other, from the positions shown in FIG. 2 to the positions shown in FIG. 5 and vice versa. When the spool 22 and shaft 20 are in the approximate position shown in FIG. 1, the cylindrical sleeve 40 and the end effectors 44a, 44b will be in the approximate position shown in FIG. 2; i.e., with the jaws open. Thus, when the spool 22 is moved towards the thumb ring 24, or vice versa, the cylindrical sleeve 40 and the end effectors 44a, 44b will be brought into the approximate position shown in FIG. 4; i.e., with the jaws closed. Moreover, it will also be appreciated that it is preferable to move the thumb ring 24 relative to the spool 22, rather than vice versa since that will move the cylindrical sleeve 40 relative to the end effectors 44a, 44b rather than vice versa. This is desirable so that the end effectors are not moved away from a tissue sample while the jaws are being closed.

Turning now to FIGS. 7a through 7e, the operation of the multiple sample bioptome of the invention is illustrated schematically in sequence. As seen in FIG. 7a, a first tissue sample is taken by positioning the jaw cups 46a, 46b around a tissue 60 to be sampled. The handle 12 of the bioptome 10 is operated as described above so that the cylindrical sleeve 40 is moved distally over the narrow arms 50a, 50b of the jaw assembly 44 to the position approximately shown in FIG. 7b. When the sleeve 40 is moved toward this position, the jaw cups 46a, 46b are brought close to each other and the sharp rims 48a, 48b of the jaw cups 46a, 46b engage the tissue 60 and bite into it. Contemporaneously, and as seen with reference to FIGS. 7f–7h, the knife sharp edge 42 of the sleeve 40 severs any tissue 60 extending from the lateral sides of the jaw cups 46a, 46b. A first sample 60a of the tissue 60 is thereby trapped between the jaw cups 46a, 46b and severed from the tissue 60. It should be noted that while taking the bite, the coil 16 is not free to stretch, as it is kept longitudinally stiff by the shrink wrap or sheath 15 which preferably extends along the length of the coil 16. If desired, a wire can be used instead of the shrink wrap or sheath. The wire, which would typically be flat, would be attached to the proximal and distal ends of the coil to keep the coil in tension and prevent it from stretching as the sleeve is moved forward and a bite taken.

With the end effectors 44a, 44b in the position approximately shown in FIG. 7b, the multiple sample bioptome 10 may be relocated to another tissue area for sampling. The handle 12 of the bioptome 10 is operated as described above so that the cylindrical sleeve 40 is moved proximally over the narrow arms 50a, 50b of the jaw assembly 44 to the position approximately shown in FIG. 7c. When the sleeve 40 is moved towards this position, the jaw cups 46a, 46b are biased apart by the resilience in the gently bent portions 53a, 53b of their respective arms 50a, 50b. The jaw cups can then be positioned around a second tissue 61 for sampling. The procedure described above with reference to FIGS. 7a and 7b is repeated. In this instance, however, as the jaw cups 46a, 46b are brought into position, the tissue 61 pushes the first sample 60a proximally away from the jaw cups 46a, 46b and into the space between the narrow arms 50a, 50b as seen in FIG. 7c. Those skilled in the art will appreciate that the tissue sample 60a is typically gummy and pliant and will stick to and move along one or both of the narrow arms 50a, 50b of the end effectors 44a, 44b. The samples will also stick to each other. Upon the taking of a sample 61a from the tissue 61, both samples 60a and 61a are safely trapped between the narrow arms 50a, 50b of the end effectors 44a, 44b as shown in FIG. 7d. The procedure described above with reference to FIGS. 7a through 7d is then repeated as suggested in FIG. 7e until the space between the arms 50a, 50b is filled with samples 60a, 61a, etc. According to a presently preferred embodiment of the invention, four to six samples may be captured between the arms of the jaw assembly. The presently preferred dimensions of the end effectors are approximately 0.45 inch in length by approximately 0.095 in height.

FIGS. 7f–7h show a top view of the sequence of operations depicted in side views in FIGS. 7a and 7b. From the top view of FIG. 7f, it can be seen that the tissue 60 extends beyond the sides of the jaw cups 46a, 46b. The knife-sharp distal edge 42 of the cylinder 40 severs the tissue 60 which extends beyond the jaw cups so that the sample 60a can be removed from the tissue 60 as shown in FIGS. 7g and 7h.

As mentioned herein above, there are several ways other than welding in which the distal end 18a of the control wire 18 may be coupled to the cylindrical sleeve 40. In particular, FIGS. 8a through 9b show two other mechanisms for coupling the distal end of the control wire 18 with the sleeve.

As shown in FIGS. 8a and 8b, the distal end 18a of the control wire 18 is provided with a Z-bend. The side wall of the cylindrical sleeve 40 is punched with two spaced apart semicircular holes 145a, 145b leaving a bendable narrow strip 145c between them. The narrow strip 145c is bent radially inward a distance sufficient to accommodate the distal end 18a of the control wire 18. The Z-bend of the distal end 18a of the control wire 18 is inserted through the space formed between the narrow strip 145c and the semicircular holes 145a, 145b as shown in FIGS. 8a and 8b.

As shown in FIGS. 9a, and 9b, the side wall of the cylindrical sleeve 40 is punched with a first hole 245a and a second hole 245c which is circumscribed by the first hole 245a. The first hole 245a is preferably rectangular, semicircular, or trapezoidal in shape to form a bendable tab 245b which is bent radially inward as shown best in FIG. 9b. The Z-bend of the distal end 18a of the control wire 18 is inserted through the second hole 245c in the bendable tab 245b as shown in FIGS. 9a and 9b.

FIGS. 10 and 10a show another embodiment of a multiple sample bioptome 310 of the invention which is particularly suited for cervical biopsy procedures or other laparoscopic biopsy procedures where the biopsy site is approachable in a relatively short and direct path rather than through the long tortuous path of the lumen of an endoscope. In this embodiment, a proximal actuation mechanism 312 is provided with a fixed handle portion 324 and a movable lever portion 322 which is coupled to the fixed handle portion 324 by a pivot pin 323. A hollow tube 340 is coupled at its proximal end to the movable lever portion 322 of the actuation mechanism 312 by a cross pin 341 or other suitable fastening means. The distal end 340a of the tube 340 is provided with a knife sharp edge 342. A relatively rigid rod 318 extends through the tube 340 and is coupled at its proximal end to the fixed handle portion 324 by means of a cross pin 319 or other suitable fastening means. The distal end 318a of the rod 318 is hollow and internally threaded with threads 370 to receive an externally threaded screw 302.

As best shown in FIG. 10a, the distal end of the rod 318 is coupled to a jaw assembly 344 which includes end effectors 344a, 344b, the screw 302, and a washer 304 In particular, the angled proximal ends 352a, 352b of the narrow arms 350a, 350b of the end effectors 344a, 344b are fastened between the washer 304 and the threaded screw 302 which is threaded into the hollow threaded distal end 318a of the rigid rod 318.

As shown in FIG. 10, the fixed handle portion 324 is provided with a lower thumb ring 324a and the movable lever portion 322 is provided with a lower finger ring 322a. The upper end 322b of the movable lever portion 322 is provided with a slot 322c for engaging the cross pin 341 and the rod 318 is provided with a slot 317 through which the cross pin passes. Those skilled in the art will appreciate that the actuation mechanism 312 is manipulated using a conventional scissors-grip. Pivotal movement of the movable lever portion 322 of the actuation mechanism 312 as indicated by the arrows 321 results in linear movement of the tube 340 as indicated by the arrows 339. It will also be appreciated that the slots 317 and 322c may be dimensioned to limit movement of the tube 340. Because of the geometry of arms 350a, 350b of the end effectors 344a, 344b, movement of the tube 340 relative to the rod 318 results in a riding of the tube 340 over the arms 350a, 350b, and an opening and closing of the jaws as described above. It should be appreciated that, if desired, the actuation mechanism 312 may be used with the flexible coil and pull wire described with reference to FIGS. 1 and 2. Conversely, the actuation mechanism 12 described with reference to FIG. 1 may be used with the tube and rod arrangement of FIG. 10. It will also be appreciated that instead of making the push rod 318 fixed in the non-moving handle 324, and the tube 340 movable with the lever 322, the push rod 318 could move, and the tube 340 could be fixed. With such an arrangement, movement of the lever relative to the handle would cause the end effectors 344a, 344b to be drawn into the tube 340, with the jaws closing, and with the jaws and the sharp end 342 of the tube 340 severing the tissue.

It will be appreciated that all of the embodiments of the multiple sample bioptome shown in FIGS. 1–10a can be provided with a cautery capability. For example, as seen in FIG. 10, a cautery contact 398 is provided which contacts the rigid rod 318 and extends out of the fixed portion 324 of the handle 312. In addition, the tube 340 is preferably provided with shrink wrap or other insulation 399. With this arrangement, when a cautery current is applied to the cautery contact 398, the jaw assembly 344 is electrified via its connection to the rod 318. Typically, cauterization would be carried out after a sample is obtained and severed from the surgical site with the jaws still located at the surgical site. Because the body of the patient acts as the second electrode (ground), current flows from the jaws into the patient at the surgical site, thereby effecting a cauterization of the surgical site rather than cauterizing the sample in the jaws.

Figure 11:
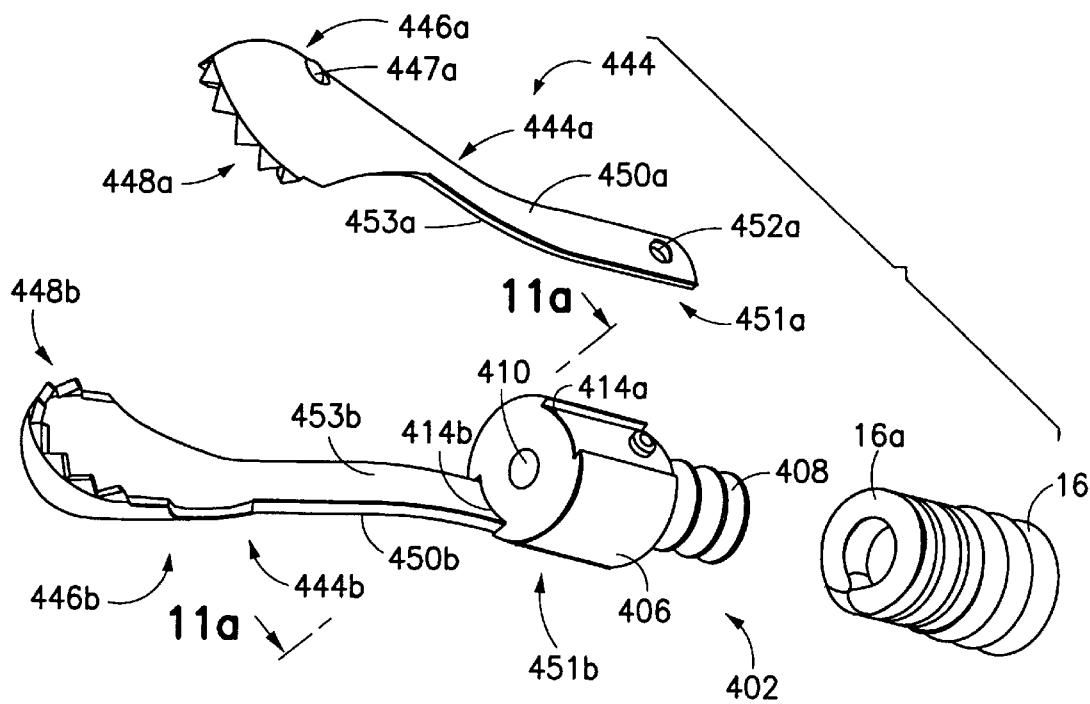
FIG. 11 is an exploded perspective view of another embodiment for mounting jaws on the distal end of a coil.
Figure 11A:
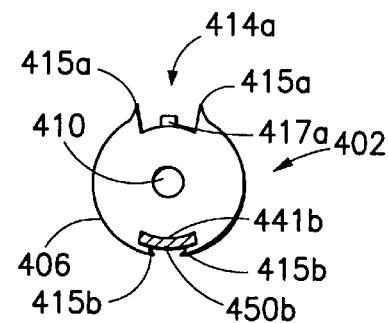
FIG. 11a is a sectional view taken along the line 11a—11a in FIG. 11.
Figure 11B:
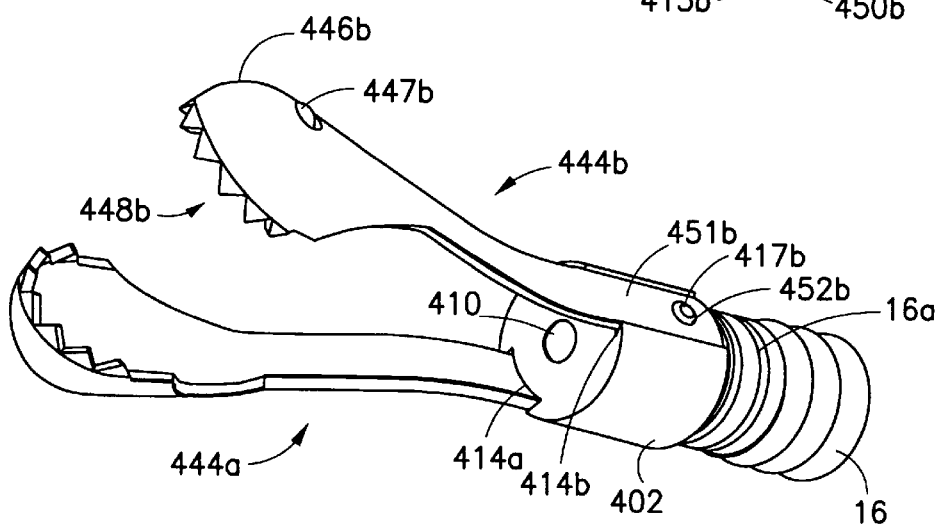
FIG. 11b is a view similar to FIG. 11 with the jaws coupled to the distal end of the coil.

Turning now to FIGS. 11, 11a, and 11b, another embodiment of a jaw assembly 444 includes a pair of end effectors 444a, 444b and a mounting screw 402 for coupling the jaws to the distal end 16a of a flexible coil 16. Each end effector 444a, 444b includes a jaw cup 446a, 446b preferably having an array of radially arranged cutting teeth 448a, 448b and a resilient, preferably narrow, arm 450a, 450b which extends proximally from the jaw cup 446a, 446b. The exterior surface of the jaw cup 446a, 446b is preferably provided with a closing cam 447a, 447b as described in co-pending co-owned application Ser. No. 08/412,058, filed Mar. 28, 1995, which is hereby incorporated by reference herein. The narrow arm 450a, 450b is provided with a mounting hole 452a, 452b at its proximal end 451a, 451b and a gently angled portion 453a, 453b. At least the gently angled portion 453a, 453b of the arms 450a, 450b, and preferably the entire arms 450a, 450b are formed from super-elastic metal such as Nitinol, and are biased apart from each other (due to angled portions 453a, 453b of the arms 450a, 450b), thereby urging the jaw cups 446a, 446b apart (as seen in FIG. 11b). In addition, as the arms 450a, 450b and the jaws 446a, 446b are preferably integral with each other, the jaws are preferably formed from a super-elastic metal.

According to the embodiment shown in FIGS. 11, 11a, and 11b, the proximal end 451a, 451b of each arm 450a, 450b is coupled to the distal end 16a of the coil 16 by crimping/locking with the hollow threaded screw 402 as best illustrated in FIGS. 11a and 11b. The threaded screw 402 is substantially cylindrical, and generally includes a head portion 406, a threaded portion 408, and a cylindrical throughbore 410 along its central axis. The throughbore 410 is dimensioned to receive and allow lateral movement of the control wire 18 as described above with reference to FIGS. 5–7. The head portion 406 has a diameter substantially equal to that of the outer diameter of the coil 16, and is provided with two opposed grooves 414a, 414b on the outer perimeter of the head portion 406. The grooves 414a, 414b are provided with side peaks 415a, 415b and a raised pin 417a, 417b, and are dimensioned to receive the proximal ends 451a, 451b of each of the narrow arms 450a, 450b. The proximal ends 451a, 451b of the arms 450a, 450b are placed in the respective grooves 414a, 414b so that the pins 417a, 417b engage respective mounting holes 452a, 452b. The pins 417a, 417b are flattened like rivets and the peaks 415a, 415b of the grooves are folded over the arms as shown best in FIGS. 11a and 11b. The threaded portion 408 of the hollow screw 402 has a diameter substantially equal to the inner diameter of the coil 16 and threadably engages the interior of the distal end 16a of the coil 16 as shown in FIG. 11b.

FIGS. 12 and 12a–12c, show yet another embodiment of mounting jaws at the distal end of a flexible coil. A jaw assembly 544 includes a pair of end effectors 544a, 544b and a mounting screw 502 for coupling the jaws to the distal end 16a of a flexible coil 16. Each end effector 544a, 544b includes a jaw cup (not shown) which is substantially the same as any of the previously described embodiments, and a resilient, preferably narrow, arm 550a, 550b which extends proximally from the jaw cup. The narrow arm 550a, 550b is provided with semi-cylindrical portion 552a, 552b at its proximal end 551a, 551b which terminates with a pair of proximally extending tabs 553a, 553b, 555a, 555b.

According to the embodiment shown in FIGS. 12 and 12a–12c, the proximal end 551a, 551b of each arm 550a, 550b is coupled to the distal end 16a of the coil 16 with the hollow threaded screw 502 as best illustrated in FIGS. 12b and 12c. The threaded screw 502 is substantially cylindrical, and generally includes a head portion 506, a threaded portion 508, and a cylindrical throughbore 510 along its central axis. The throughbore 510 is dimensioned to receive and allow lateral movement of the control wire 18 as described above with reference to FIGS. 5–7. The distal end of the head portion 506 has a diameter substantially equal to that of the outer diameter of the coil 16, and is provided with two pair of opposed grooves 514a, 514b, 516a, 516b on the outer perimeter of the head portion 506. The grooves are dimensioned to receive the proximal ends 551a, 551b of each of the narrow arms 550a, 550b, as shown best in FIGS. 12b and 12c, with the semi-cylindrical portions 552a, 552b lying on the reduced diameter proximal portion of the head 506, the tabs 553a, 553b residing in the groove 516a, and the tabs 555a, 555b residing in the groove 516b. The threaded portion 508 of the hollow screw 502 has a diameter substantially equal to the inner diameter of the coil 16 and threadably engages the interior of the distal end 16a of the coil 16 as described above.

FIGS. 13, 13a, and 13b show a presently preferred embodiment of coupling a jaw assembly to the distal end of a coil. According to this embodiment, the jaw assembly 560 includes a pair of end effectors 562a, 562b, a mounting screw 564, and a retaining sleeve or washer 566. Each end effector 562a, 562b includes a jaw cup 568a, 568b and a resilient, preferably narrow, arm 570a, 570b which extends proximally from the cup. The proximal end of each arm 570a, 570b is provided with a mounting hole 572a, 572b. In all other respects, the end effectors may incorporate various features of the end effectors described above. The mounting screw 564 is similar to the mounting screw 402 described above. It is substantially cylindrical, having a head portion 564a, a threaded portion 564b, a through bore 564c, and a pair of diametrically opposed arm receiving grooves 564d, 564e, each of which is provided with an upstanding pin 564f, 564g. In this embodiment, a proximal portion 564h of the screw head 464a has a reduced diameter which is substantially equal to the inner diameter of the retaining sleeve or washer 566. The upstanding pins 564f, 564g are located on this proximal portion 564h of the screw head 564a. From the foregoing, those skilled in the art will appreciate that the end effectors 562a, 562b are coupled to the screw 564 by placing respective arms 570a, 570b in the grooves 546d, 564e so that the respective mounting holes 572a, 572b are engaged by the respective pins 564f, 564g. After the arms are so arranged relative to the screw, the sleeve or washer 566 is placed over the proximal portion 564h of the screw head 464a and the proximal ends of the arms are captured between the sleeve and the screw head. The threaded portion 564b, of the screw is then coupled to the distal end of a coil (not shown) as described above and the sleeve or washer 566 is captured between the coil and the screw head as described above.

As mentioned above, the jaw cups are opened and closed by movement of a cylindrical sleeve which is coupled to a control wire. FIGS. 14, 14a, and 14b show another embodiment of a cylindrical sleeve 640 coupled to the distal end 618a of a control wire 618 for opening and closing a jaw assembly 644 which is coupled to the distal end 16a of a flexible coil 16. The jaw assembly 644 is substantially the same as any of the various jaw assemblies described above. Notably, the jaw assembly has two relatively narrow spaced apart arms 650a, 650b. According to the embodiment of FIGS. 14, 14a, and 14b, a cross member 628 is coupled to the distal end 618a of the control wire 618. The cross member 628 is a disk segment having two opposite substantially parallel sides 628a, 628b, two curved sides 268c, 628d having radii of curvature which correspond to the inner radius of the cylindrical sleeve 640, and a central bore 628e. The distance between the parallel sides 628a and 628b is less than the distance between the interior surfaces of the arms 650a, 650b of the jaw assembly; and the distance between the curved sides 628c and 628d is substantially equal to the interior diameter of the cylindrical sleeve 640. The diameter of the bore 628e is substantially equal to the diameter of the control wire 618. The control wire 618 is coupled to the cross member 628 by inserting the distal end 618a of the control wire through the bore 628e and crimping the control wire on either side of the cross member as shown best in FIGS. 14 and 14a. The cross member 628 is aligned relative to the jaw assembly 644 so that it extends freely between the arms 650a and 650b as seen best in FIGS. 14a and 14b. The cylindrical sleeve 640 is coupled to the cross member 628 by crimping the sleeve on either side of the cross member 628 at 699 as seen best in FIG. 14a.

There have been described and illustrated herein several embodiments of an endoscopic multiple sample bioptome. While particular embodiments of the invention have been described, it is not intended that the invention be limited thereto, as it is intended that the invention be as broad in scope as the art will allow and that the specification be read likewise. Thus, while the jaw assembly has been disclosed as being formed from a particular super-elastic metal, it will be understood that other super-elastic alloys can be used to achieve the same or similar function as disclosed herein. For example while the jaws have been disclosed as made out of a nickel-titanium alloy, they may also be made out of, e.g., iron-platinum, silver-cadmium, nickel-aluminum, manganese-copper, copper-zinc, nickel-thallium, or any other super-elastic alloy. It will furthermore be appreciated that while the apparatus of the invention was described as advantageously permitting the obtaining of multiple biopsies without removal from the surgical site, the apparatus of the invention, if desired, could still be used for obtaining single biopsies at a time. In fact, the endoscopic instrument need not be used for taking biopsies at all, but could be used as a dissector. In a dissector embodiment, the tube which causes the arms to close would not have a sharp end, and the end effectors could be paddle or otherwise shaped rather than having jaw cups. Moreover, while particular configurations of the actuation mechanism of the invention have been disclosed, it will be appreciated that other types of actuation mechanisms could be utilized. Also, while specific couplings of the ends of the coil and control wire have been shown, it will be recognized that other types of couplings could be used with similar results obtained. Similarly, while specific couplings of the ends of the rigid tube and rod have been shown, it will be understood that other types of couplings could be used. Moreover, while particular configurations have been disclosed in reference to the jaw assembly, it will be appreciated that other configurations could be used as well. For example, while it is preferred to provide jaws with sharp edges, it will be appreciated that in lieu of edges, the jaws can be provided with sharp teeth which, in conjunction with the sharp cylinder, will provide a cutting ability. Furthermore, while in the second embodiment the inner rod is shown to be stationary and the outer tube is shown to be adjustable, the outer tube may be made stationary and the rod adjustable. It will therefore be appreciated by those skilled in the art that yet other modifications could be made to the provided invention without deviating from its spirit and scope as so claimed.

We claim:

1. An endoscopic instrument having proximal and distal portions, comprising:
    a) a hollow tube member having a proximal end and a distal end;
    b) first and second end effectors each having arms biased away from each other, each of said arms being coupled to said distal end of said hollow tube member;
    c) a cylindrical member slidably disposed over said distal end of said hollow tube member;
    d) an actuator having a proximal end and a distal end, said actuator extending through said hollow tube member; and
    e) coupling means for coupling said distal end of said actuator to said cylindrical member for causing said cylindrical member to move relative to said first and second end effectors so as to cause said cylindrical member, in a first position, to extend over at least a portion of said first and second end effectors so as to force said arms of said first and second end effectors toward each other and assume a relatively closed position, and, in a second position, to permit said first and second end effectors to extend away from each other and assume a relatively open position, wherein,
    said coupling means comprises a disk segment coupled to said distal end of said actuator, said disk segment being coupled to said cylindrical member by a crimp in said cylindrical member.

2. An endoscopic instrument according to claim 1, wherein:
    said disk segment has two substantially parallel sides and two curved sides, said two curved sides being coupled to said cylindrical member.

3. An endoscopic instrument according to claim 2, wherein:
    said disk segment passes between said arms of said first and second end effectors.

4. An endoscopic instrument according to claim 1, wherein:

said disk segment has a central through bore, said distal end of said actuator extends through said through bore and is crimped on opposite sides of said through bore.

5. An endoscopic instrument according to claim 1, wherein:

said hollow tube member comprises a coil.

6. An endoscopic instrument according to claim 1, wherein:

said first and second end effectors each include a jaw cup.

7. An endoscopic instrument according to claim 1, wherein:

said actuator comprises a wire extending through said hollow tube member and coupled to said disk segment, and handle means coupled to said wire and to said tube member, said handle means for moving said wire relative to said tube member.

8. An endoscopic instrument according to claim 1, wherein:

said arms are made from a superelastic metal.

* * * * *